United States Patent
Zacharopoulos (10) Patent No.: US 10,252,084 B2
(45) Date of Patent: Apr. 9, 2019

(54) OPTICAL WATER SURFACE DETECTOR AND METHOD

(71) Applicant: AKTINA CORP., Congers, NY (US)

(72) Inventor: Nicholas G. Zacharopoulos, New City, NY (US)

(73) Assignee: AKTINA CORP., Congers, NY (US)

( * ) Notice: Subject to any disclaimer, the term of this patent is extended or adjusted under 35 U.S.C. 154(b) by 0 days.

(21) Appl. No.: 15/353,267

(22) Filed: Nov. 16, 2016

(65) Prior Publication Data

US 2017/0136262 A1   May 18, 2017

Related U.S. Application Data

(60) Provisional application No. 62/255,563, filed on Nov. 16, 2015.

(51) Int. Cl.
*G01J 5/02* (2006.01)
*A61N 5/10* (2006.01)
*G01T 1/169* (2006.01)
*G01F 23/292* (2006.01)

(52) U.S. Cl.
CPC ....... *A61N 5/1075* (2013.01); *G01F 23/2928* (2013.01); *G01T 1/169* (2013.01); *A61N 2005/1076* (2013.01)

(58) Field of Classification Search
CPC ............................. G01T 1/169; G01F 23/2928
See application file for complete search history.

(56) References Cited

U.S. PATENT DOCUMENTS

| | | | | |
|---|---|---|---|---|
| 2002/0106972 A1* | 8/2002 | Lebel | .................... | H01L 21/681 451/5 |
| 2004/0039486 A1* | 2/2004 | Bacchi | ................ | H01L 21/6838 700/275 |
| 2007/0014928 A1* | 1/2007 | Delaperriere | ........... | G01T 1/169 427/372.2 |
| 2008/0164416 A1* | 7/2008 | Safai | ....................... | G01T 1/202 250/366 |
| 2008/0246974 A1* | 10/2008 | Wilson | .................... | G01B 11/24 356/634 |
| 2009/0224784 A1* | 9/2009 | Pagani | ................ | G01R 31/3172 324/762.02 |
| 2010/0019137 A1* | 1/2010 | Torre | ....................... | G01T 1/169 250/252.1 |
| 2010/0243875 A1* | 9/2010 | Plompen | .................. | G01T 1/169 250/252.1 |

* cited by examiner

*Primary Examiner* — Kiho Kim
(74) *Attorney, Agent, or Firm* — Donald J. Ranft; Collen (57) ABSTRACT

A device and method to be used in the calibration process for a linear accelerator (LINAC). The optical water surface detector device allows the accurate determine of the height of the water surface in a tank. The device housing includes a light source and a light receiver. The housing can also include a circuit board. The device is mounted on an arm attached to a vertical position mechanism mounted within the tank. The light source within the device is controlled by a main control unit which also receives signals from the receiver and determines the amount of light striking the receiver. The control unit also controls the position of the vertical position mechanism and thus the arm on which the device is mounted.

25 Claims, 10 Drawing Sheets

OPTICAL WATER SURFACE DETECTOR AND METHOD

CROSS-REFERENCE TO RELATED APPLICATION

This non-provisional application claims priority from pending provisional Application No. 62/255,563 filed in the United States Patent and Trademark Office on Nov. 16, 2015.

BACKGROUND OF THE INVENTION

Figure 1:
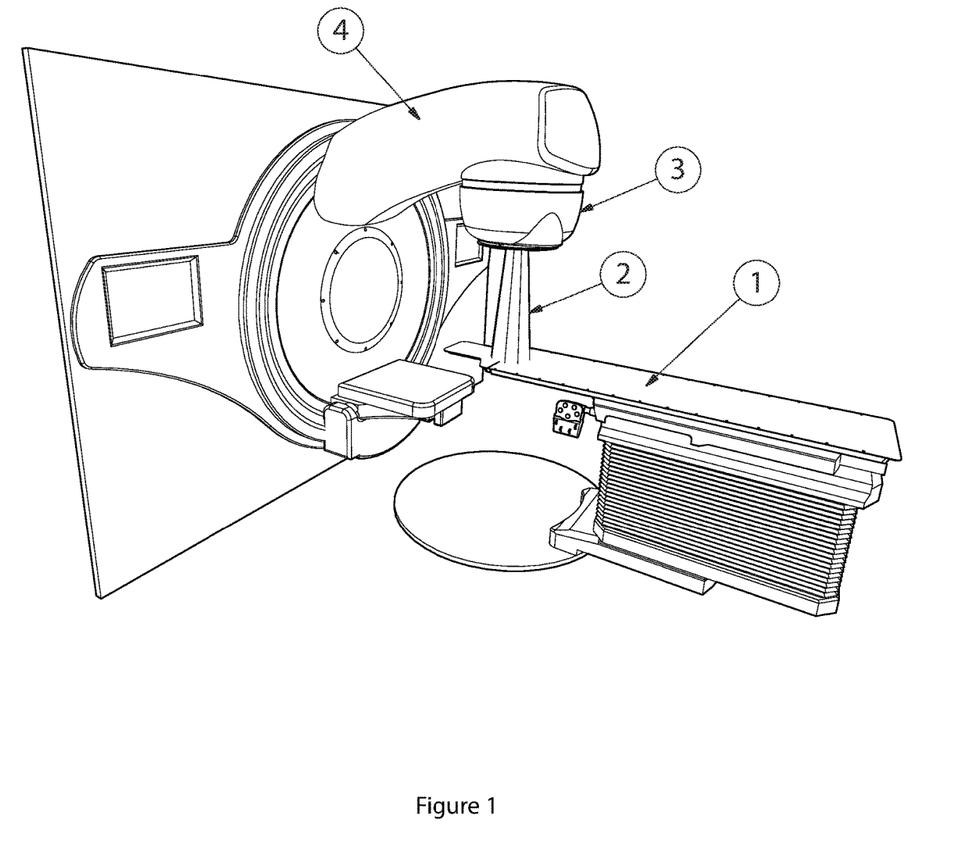
FIG. 1 is depicts a typical medical linear accelerator

A medical linear accelerator (LINAC) is a common tool used within oncology community in the fight against cancer. (FIG. 1) These devices deliver targeted radiation to the tumor sight in an accurate and reproducible manner. Routine quality control (QC) is required on the LINAC to ensure that (A) the LINAC is delivering the correct amount of radiation and (B) the LINAC is directing the radiation to the correct location within the patient.

Figure 2:
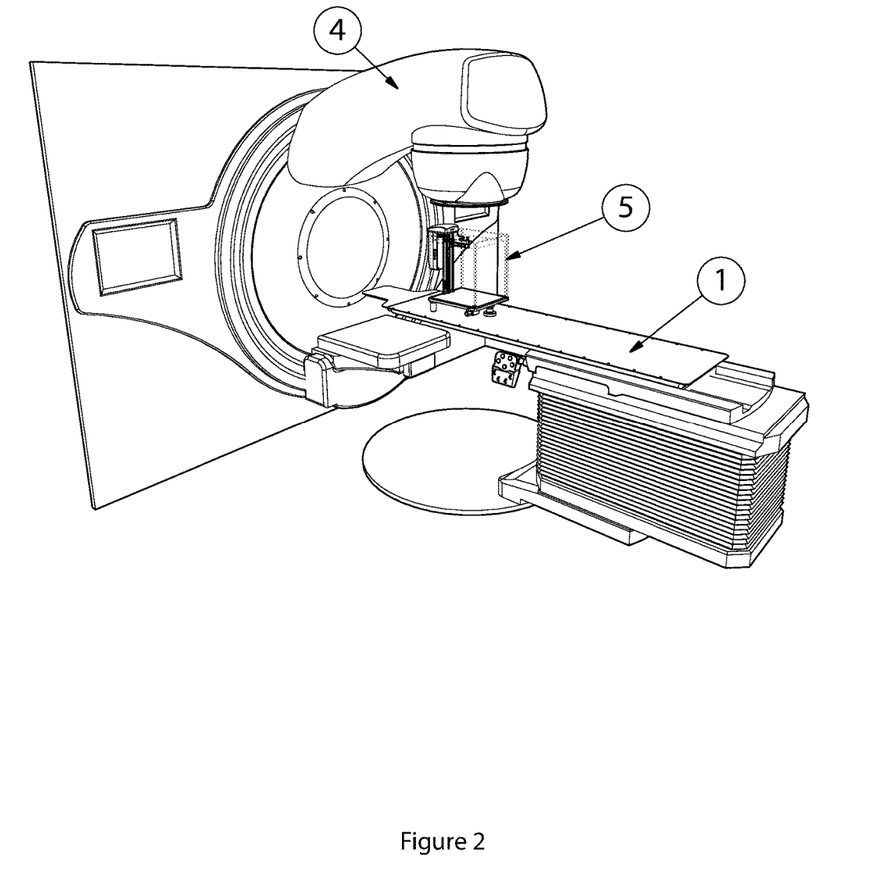
FIG. 2 is a linear accelerator showing setup location for the QC water phantom (item 5).

The tests that are used to monitor the amount of radiation given typically involve measuring the radiation output delivered to a device that simulates the patient. These devices, referred to as phantoms, are usually water filled tanks with robotics that position a radiation measuring sensor at various predefined depths within the water. The phantom is typically positioned within the radiation beam at a configuration and distance as shown on FIG. 2.

Figure 3:
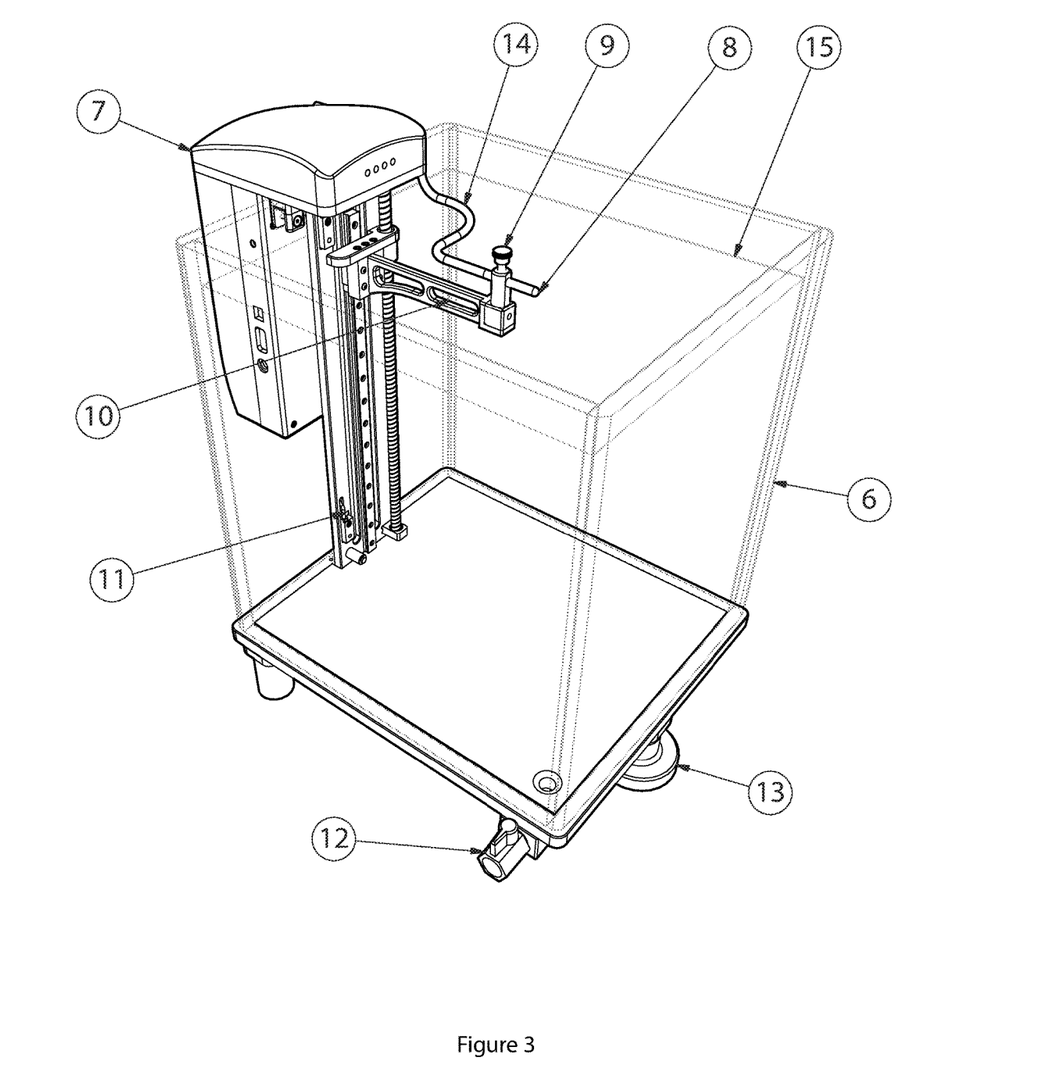
FIG. 3 depicts a typical water phantom.

A typical water phantom is shown on FIG. 3. The water phantom typically consists of a water tank (6) with leveling feet (13) and a water drain valve (12) at its bottom. An arm (10) whose height is controlled by a drive mechanism (11) in the tank controls the height of an arm on which a holder (9) houses a radiation detector (8). A microprocessor is included in the main unit (7).

Figure 4:
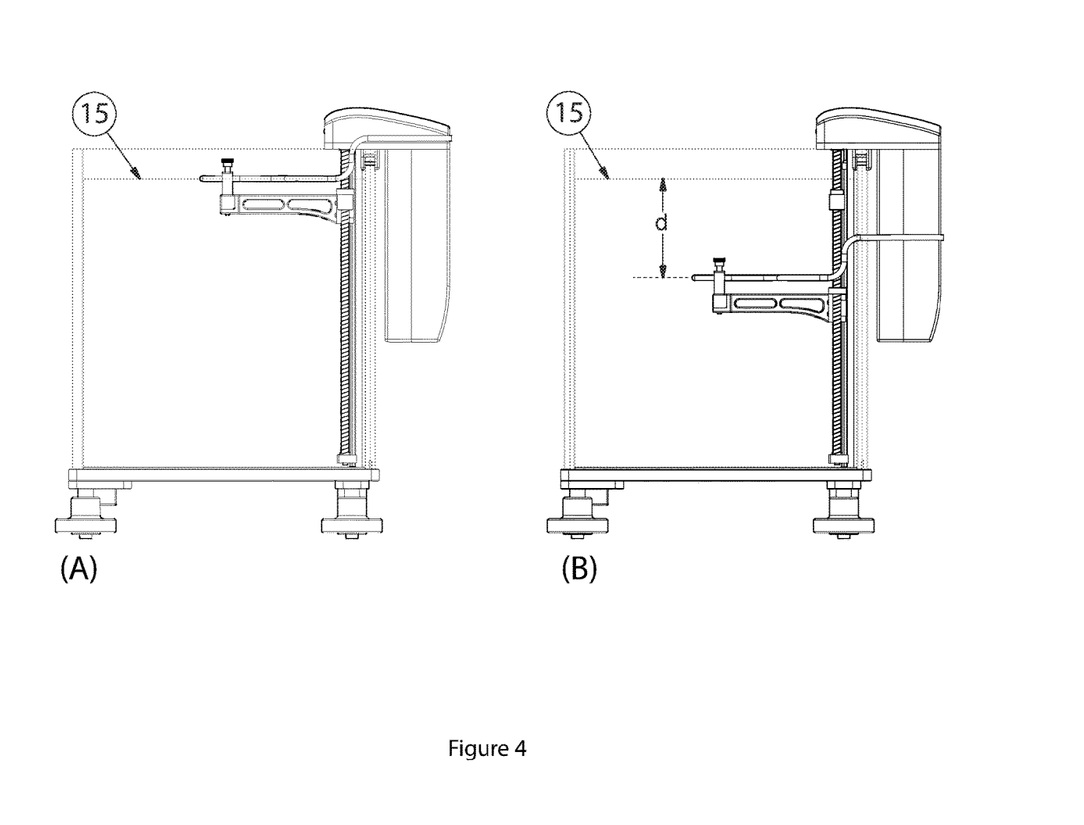
FIGS. 4(A) and 4(B) are side views of the phantom showing traditional chamber setup for testing to water surface (15). In view (A) the center of the chamber is aligned to the water surface by eye and a zero position is defined. In view (B) the chamber is shown positioned to depth d downwards from the zero position defined in previous step. The chamber should be at the correct distance d from the water surface, which is critical to making an accurate reading.
Figure 5:
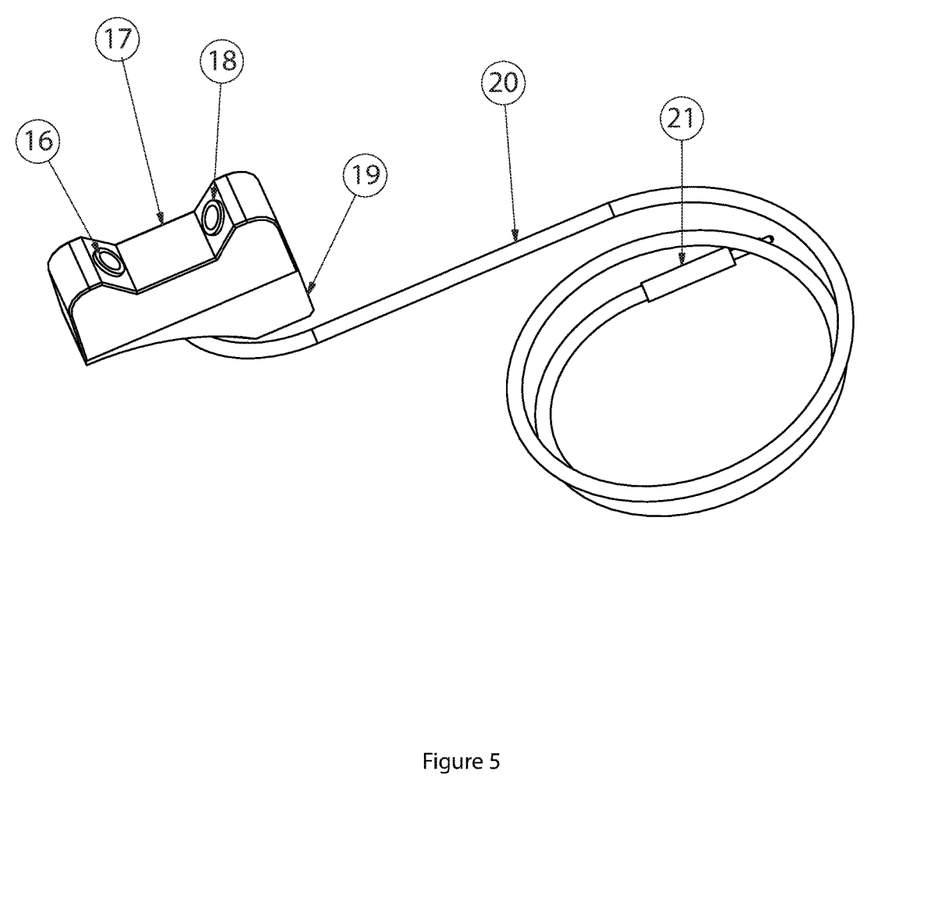
FIG. 5 is a top view of auto-surface finder

Taking radiation measurements with a water phantom shown on FIG. 3 requires positioning the radiation detector at very accurate depths within the water. If the radiation detector is at the wrong depth, even by a fraction of a millimeter, the reading will be wrong. This would ultimately adversely affect the patient's treatments. To position the typical existing detector at the correct depth, a two-step process shown on FIG. 4 is used:

(A) The user adjusts the height of the motorized arm until the radiation detector (8) is positioned such that the water surface is at the center of the radiation detector (8). This established a zero point.
(B) the user then adjusts the depth of the detector with the aid of the motorized positioning system to position the radiation detector precisely at depth D.

Step A is very subjective and difficult to accomplish accurately due mainly to water meniscus and parallax effects. The subjective nature of the process means that users typically double and triple check their work to ensure that no errors have been made. But this extra effort may not result in the true surface and it increases the time required for positioning the chamber.

SUMMARY OF THE INVENTION

The optical water surface detector presented solves this problem by providing a device and method to precisely locate the surface of the water in a completely automated method without disturbing the water surface. This is done by using the light reflected off the bottom of the water surface to identify a distance d below the surface of the water. This device and method completely removes the technician's subjectivity from the process and achieves a level of accuracy which is not possible via existing manual techniques.

PART NUMBERS

1. Treatment couch and patient support system
2. Projection of radiation beam
3. Beam collimation system
4. LINAC gantry
5. Water tank phantom
6. Walls of water tank phantom
7. Main control unit with microprocessor and control system
8. Radiation sensitive area of radiation detector
9. Holder for radiation detector
10. Arm
11. Positioning mechanism
12. Water release spigot
13. Leveling feet
14. Cable of radiation detector which connects to electrometer (not shown and not part of the water tank)
15. Water surface
16. Light source transmitter assembly
17. Upper body
18. Light detecting receiver assembly
19. lower body
20. Signal and power cable.
21. Signal and power connector
22. Light source
23. Transmitter lens
24. Receiver lens
25. Light source
26. Circuit board
27. LED current limiting resistor
28. Grommet
29. Transmitter housing 30. Receiver housing

DETAILED DESCRIPTION

Figure 6:
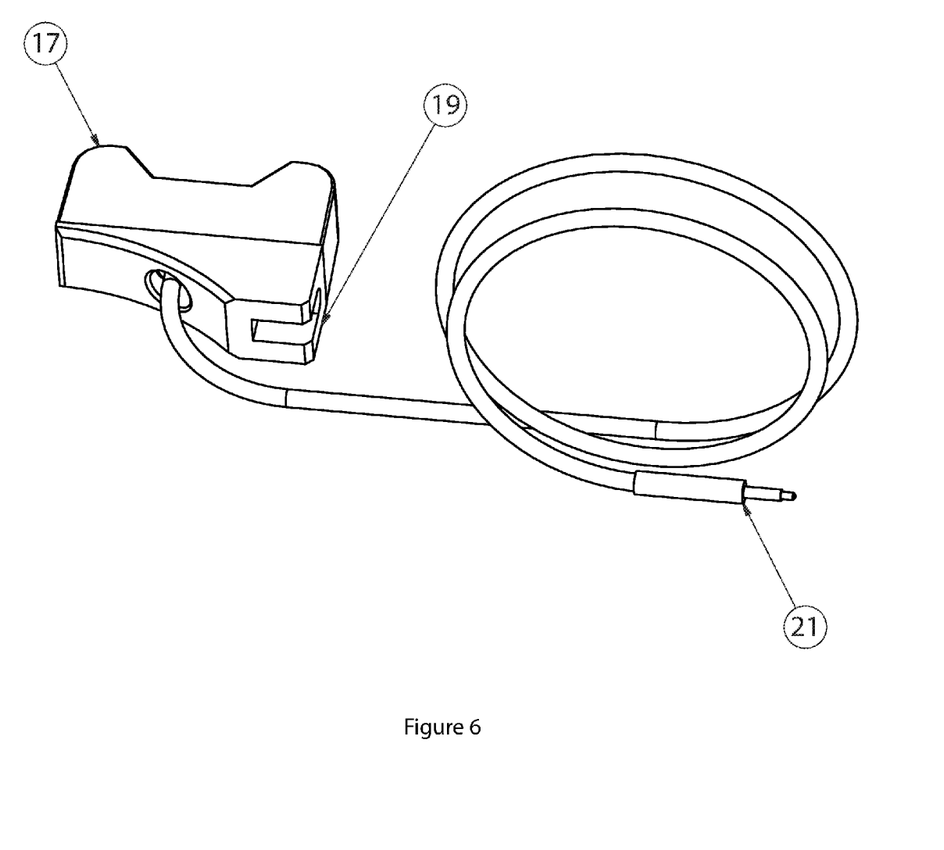
FIG. 6 is a bottom view of auto-surface finder

As shown on FIG. 6 the optical water surface detector consists of a light source, such as an infra-red transmitter, assembly (16) and a corresponding light detector receiver (light receiver) assembly (18) that is housed within a light and receiver housing. The light and receiver unit can be a single unit or comprised of an upper body (17) and lower body (19) as shown on the figures. The optical water surface detector device is mounted on an arm (10) attached to a positioning mechanism (11) within a water tank such as a water tank phantom (5).

A main control unit is typically mounted on the tank but can be mounted separate from the water tank. The device is connected to a microprocessor located in the main control unit (7) via a signal cable (20) and connector (21). The main control unit controls the positioning mechanism and the optical water surface detector. A mechanism, such as leveling feet (13), is provided on the water tank to ensure the tank is level. And a level cane be mounted on the tank.

Figure 7:
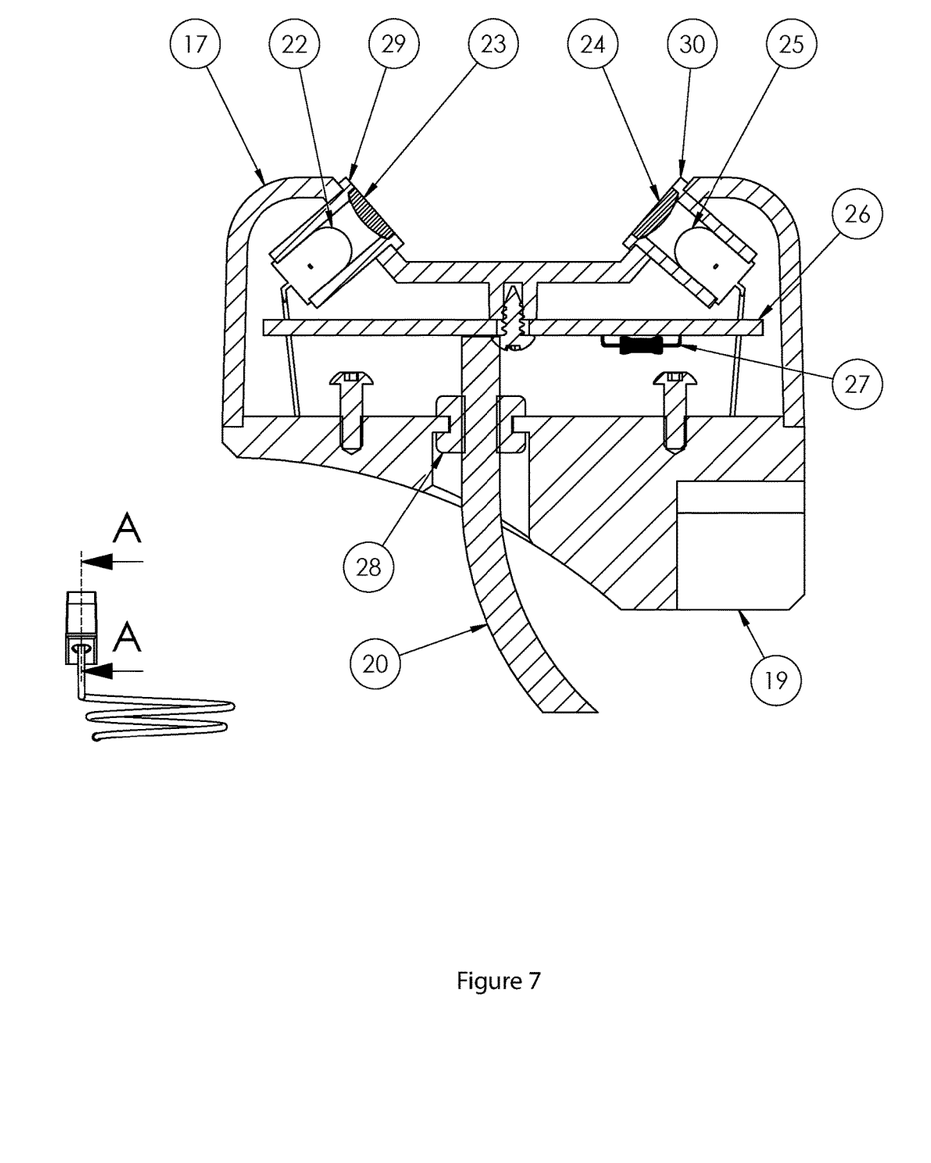
FIG. 7 is a section view of auto surface finder.

A cross section through the transmitter and receiver assemblies is shown on FIG. 7. A light source transmitter (22), such as an infra-red light emitting diode (LED), is housed within a water tight cylinder housing (29). A transmitter lens (23) may be mounted on top of the light source (22). A light receiver (25), such as infra-red photo diode, is housed within a water tight cylinder housing (30). A receiver lens (24) may be mounted on top of the light receiver (25). The light source (22) and light receiver (25) are connected to a circuit board (26) which communicates with a microprocessor in the main control unit. The circuit board transmits and receives signals via a transmission apparatus communicating with the main control unit (7).

In another embodiment the light source (22) and light receiver (25) are connected to directly to the main control unit via a transmission apparatus.

The transmission apparatus can be a cable (20) or utilize a wireless transmission device such as blue tooth or Wi-Fi. The main control unit controls the light source transmitter by turning it on and off. And the main control unit includes an analog to digital converter and measures the output of the light receiver.

Figure 8:
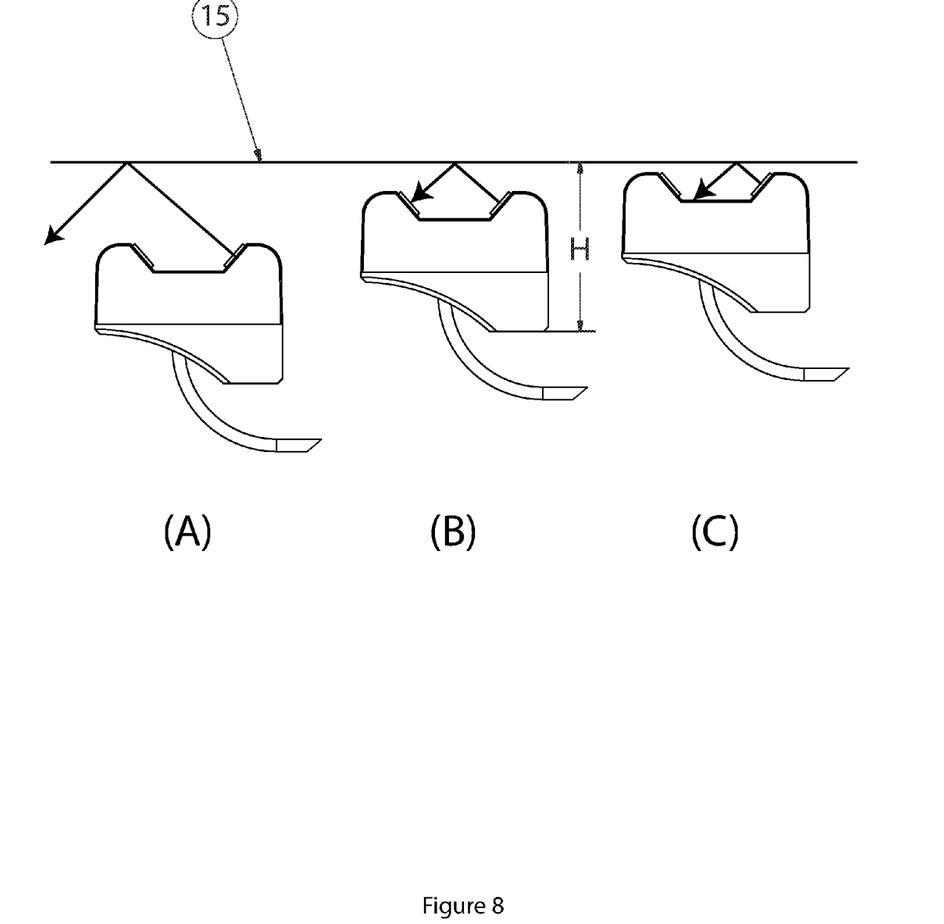
FIG. 8 depicts the light path for three scenarios: (A) when the detector is below the optimal signal point and the light is reflected beyond the receiver, (B) when the device is at the optimal depth below the water (H) the light is reflected into the receiver, and (C) when the device is higher than the optimal location and the light is reflected below the receiver.
Figure 9:
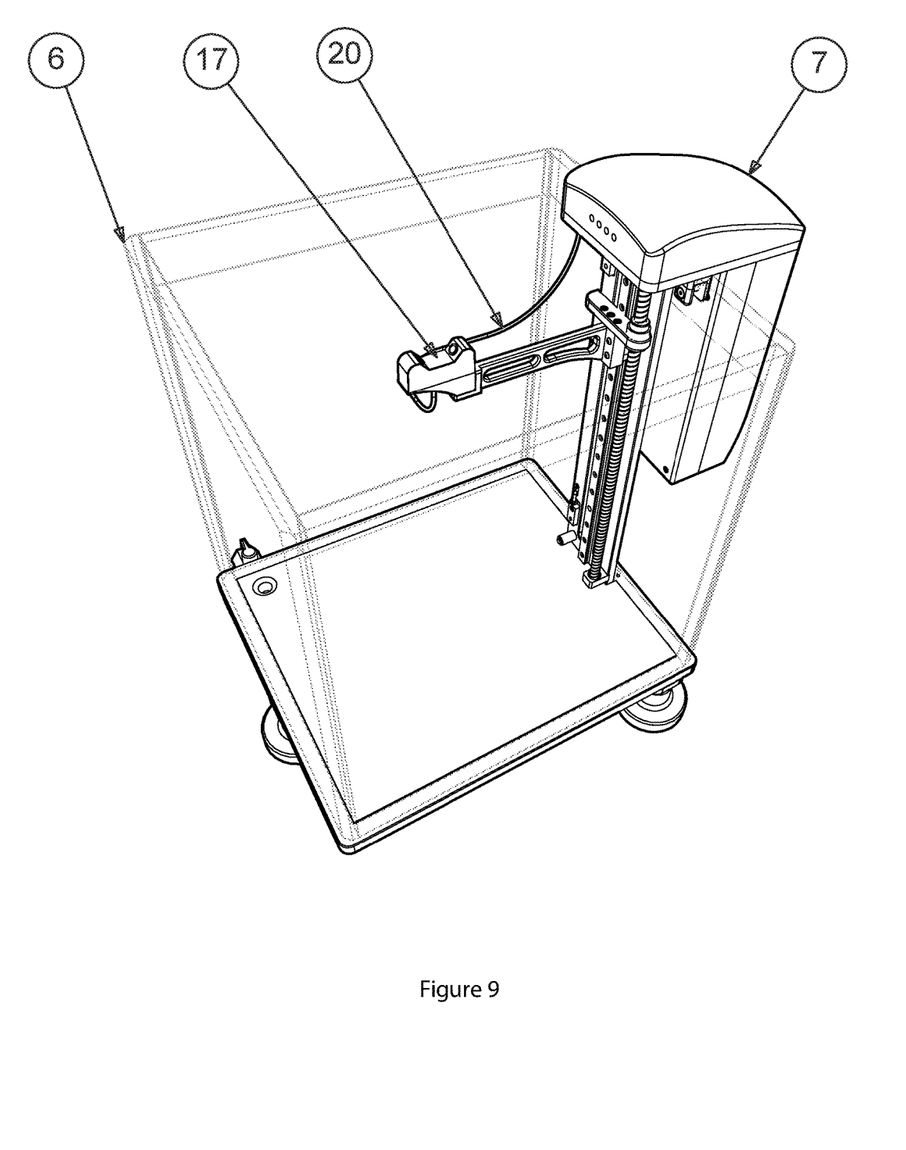
FIG. 9 depicts the optical surface detector shown assembled within the phantom.

The device works on the premise that for a particular optical water surface detector device as shown on FIG. 8 there is only one distance from the water surface at which the maximum light will be detected by the receiver (25). When the device is at the depth corresponding to this one distance, the maximum amount of light from the light source (22) will reflect off the bottom of the water surface and travel into the receiver. At other depths, a smaller portion of light will be reflected into the receiver resulting in a smaller signal being collected. As shown on FIG. 8 if the surface of the water is not at the geometrical crossing of the light path form the transmitter and the light path to the receiver, then the receiver will receive none or less light.

To use the device, the receiver signal is monitored as the device's vertical position is moved in relation to the water surface. The location where the receiver signal is greatest indicates that the device is positioned at a "sweet spot" where the maximum amount of light is reflected from the underside of the water surface into the receiver (25). When the device is at this "sweet spot" the vertical position of the device in relation the water tank can be identified. Based on the identification of the sweet spot the height of the water surface within the tank can be determined. This then allows the arm to be accurately moved as required for the radiation detector which will be mounted on the arm. By knowing the distance (H) (shown on FIG. 8) between a reference point on the device and geometrical intersection of the transmitter-receiver pair, when can cross-correlate the location of maximum signal to determine the location of the water surface relative to the device.

Figure 10:
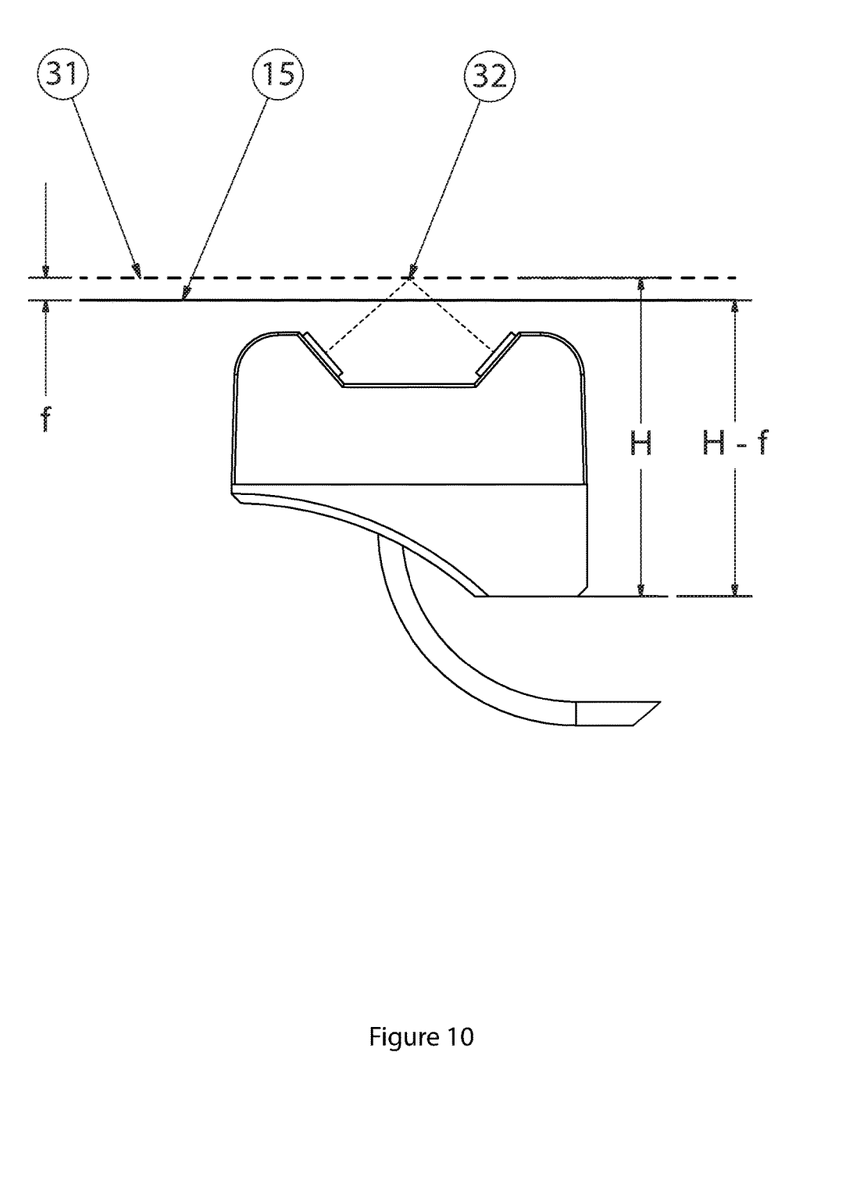
FIG. 10 illustrates distances to be measured during calibration of the device.

Due to manufacturing tolerances, the maximum signal may not correlate to the exact geometric intersection of the transmitter and receiver. The maximum signal may be correlated to a distance (f) below or above the geometric intersection of the transmitter and receiver (32). The optical water surface detector device should be calibrated by determining the distance (f). This can be accomplished by introducing highly reflective rigid surface within the water. The location of this rigid surface, unlike the water surface, can be accurately determined with standard measurement tools and techniques. Factory device calibration would then include scanning the device upwards towards the rigid reflective surface until the maximum signal is measured (H-f) by the microprocessor. This device specific offset value (H-f) can then be saved within the microprocessor memory and later used when the user scans for water surface level during normal use.

An optical water surface detector assembly comprises a light source and the light receiver connected to a circuit board with all components installed in an enclosure/housing. The housing is mounted on an arm attached to a positioning mechanism. A cable or wireless device serves as the transmission apparatus for communications with the main control unit.

In another embodiment the radiation detector is mounted on the optical water surface detector device. In such an embodiment the light source, light receiver and circuit board can be designed for removal or shielding added to avoid being exposed to radiation. In another embodiment a radiation detector can be mounted on the arm separate from the device to avoid radiation exposure with the device designed for removal without disturbing the radiation detector.

A method for detecting the water surface in a water tank is as follows:
  selecting an optical water surface detector comprising: a light source; a light receiver; the light source and the light receiver connected to a circuit board; a housing containing the light source, light receiver, and the circuit board; wherein the optical water surface detector is mounted on an arm which is attached to a positioning mechanism within a water tank and a transmission apparatus communicating between the optical water surface detector and a main control unit;
  turning on the light source;
  using the positioning mechanism to move the optical water surface detector to the position at which the control unit indicates the maximum light striking the light receiver; and
  identifying the position of the arm when the maximum light is striking the light receiver.

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

I claim the following:

1. A system comprising:
an optical water surface detector configured to detect a water surface comprising a light source; a light receiver; and a watertight housing containing the light source, and the light receiver; wherein the optical water surface detector is mounted on an arm which is attached to a positioning mechanism within a water tank and a transmission apparatus communicating between the optical water surface detector and a main control unit.

2. The optical water surface detector according to claim 1 wherein the water tank is a water tank phantom with the main control unit mounted on the water tank phantom.

3. The optical water surface detector according to claim 2 wherein the light source is infra-red.

4. The optical water surface detector according to claim 1 wherein the light source is infra-red.

5. The optical water surface detector according to claim 1 wherein the transmission apparatus is a cable.

6. The optical water surface detector according to claim 1 wherein the transmission apparatus is a wireless device.

7. The optical water surface detector according to claim 1 further comprising a circuit board located within the watertight housing to which the light source and the light receiver are connected.

8. The optical water surface detector according to claim 7 wherein the light source is infra-red.

9. The optical water surface detector according to claim 8 wherein the main control unit is mounted on the water tank.

10. The optical water surface detector according to claim 7 wherein the transmission apparatus is a cable.

11. The optical water surface detector according to claim 7 wherein the transmission apparatus is a wireless device.

12. The optical water surface detector according to claim 1 further comprising a radiation detector mounted on the optical water surface detector.

13. A system comprising: an optical water surface detector assembly configured to detect a water surface comprising a light source; a light receiver; the light source and the light receiver connected to a circuit board; a watertight housing containing the light source, the light receiver, and the circuit board; a positioning mechanism within a water tank; an arm mounted on the positioning mechanism; and a cable serving as a transmission apparatus communicating between the optical water surface detector assembly and a main control unit.

14. The optical water surface detector assembly according to claim 13 wherein the water tank is a water tank phantom.

15. The optical water surface detector assembly according to claim 14 further comprising a lens on the light receiver.

16. The optical water surface detector assembly according to claim 13 wherein the light source is infra-red.

17. The optical water surface detector assembly according to claim 16 wherein a wireless device serves as the transmission apparatus.

18. The optical water surface detector assembly according to claim 13 wherein a wireless device serves as the transmission apparatus.

19. A method for detecting a water surface in a water tank comprising:
selecting an optical water surface detector comprising: a light source; a light receiver; the light source and the light receiver connected to a circuit board; a housing within the water tank containing the light source, light receiver, and the circuit board; and a transmission apparatus communicating between the optical water surface detector and a main control unit;
turning on the light source;
moving the optical water surface detector to a position at which the control unit indicates a maximum light striking the light receiver; and
identifying a position of the optical water surface detector in relation to the water tank when the maximum light is striking the light receiver.

20. The method for detecting the water surface in a water tank according to claim 19 wherein the optical water surface detector is mounted on an arm attached to a positioning mechanism within the water tank.

21. The method for detecting the water surface in a water tank according to claim 20 wherein the light source is infra-red.

22. The method for detecting the water surface in a water tank according to claim 20 further comprising a lens on the light receiver.

23. A method for detecting a water surface in a water tank comprising:
selecting an optical water surface detector comprising: a light source; a light receiver; a watertight housing within the water tank containing the light source, the light receiver, and a transmission apparatus communicating between the optical water surface detector and a main control unit;
turning on the light source;
moving the optical water surface detector to a position below the water surface at which the control unit indicates a maximum light striking the light receiver; and
identifying a position of the optical water surface detector in relation to the water tank when the maximum light is striking the light receiver.

24. The method for detecting the water surface in a water tank according to claim 23 wherein the light source is infra-red.

25. The method for detecting the water surface in a water tank according to claim 23 wherein a wireless device serves as the transmission apparatus.

* * * * *